United States Patent
Mock-Knoblauch et al.

(10) Patent No.: US 7,842,302 B2
(45) Date of Patent: Nov. 30, 2010

(54) MIXTURE COMPRISING A DETERGENT AND A CO-DETERGENT

(75) Inventors: Cordula Mock-Knoblauch, Ludwigshafen (DE); Norbert Wagner, Mutterstadt (DE); Guenter Oetter, Frankenthal (DE); Ludwig Voelkel, Limburgerhof (DE); Susanne Petrovic, Eppelheim (DE); Arno Lange, Bad Duerkheim (DE); Darijo Mijolovic, Mannheim (DE); Stephan Hueffer, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 403 days.

(21) Appl. No.: 10/588,719

(22) PCT Filed: Feb. 11, 2005

(86) PCT No.: PCT/EP2005/001370

§ 371 (c)(1),
(2), (4) Date: Aug. 8, 2006

(87) PCT Pub. No.: WO2005/077513

PCT Pub. Date: Aug. 25, 2005

(65) Prior Publication Data

US 2007/0178056 A1    Aug. 2, 2007

(30) Foreign Application Priority Data

Feb. 13, 2004   (DE) ...................... 10 2004 007 473

(51) Int. Cl.
*A61K 8/02* (2006.01)
*A61K 8/00* (2006.01)

(52) U.S. Cl. .......................... 424/401; 424/59
(58) Field of Classification Search ................. 424/401, 424/59
See application file for complete search history.

(56) References Cited

U.S. PATENT DOCUMENTS

| 6,677,293 | B1 * | 1/2004 | Allgaier et al. | 510/417 |
| 2004/0171759 | A1 * | 9/2004 | Lange et al. | 525/192 |
| 2005/0090611 | A1 * | 4/2005 | Huffer et al. | 524/800 |

FOREIGN PATENT DOCUMENTS

| DE | 196 34 477 | 12/1997 |
| DE | 198 39 054 | 3/2000 |
| DE | 101 18 480 | 10/2002 |
| DE | 102 15 108 | 10/2003 |

OTHER PUBLICATIONS

Klier, John et al.,"Properties and Applications of Microemulsions", Advanced Materials, vol. 12, No. 23, pp. 1751-1757, 2000.
Eicke, Hans-Friedrich ,"Mikroemulsionen—Eine Wissenschaftliche und Anwendungstechnische Fundgrube?", SOFW-Journal, vol. 118, pp. 311-314, 1992.

* cited by examiner

*Primary Examiner*—Ling-Siu Choi
*Assistant Examiner*—Hui Chin
(74) *Attorney, Agent, or Firm*—Oblon, Spivak, McClelland, Maier & Neustadt, L.L.P.

(57) ABSTRACT

The invention relates to a mixture comprising a surfactant and a cosurfactant, the cosurfactant being an amphiphilic polymer having one or more hydrophobic subunits (A) and one or more hydrophilic subunits (B), wherein one or more hydrophobic subunits (A) have been formed on the basis of a polyisobutene block whose polyisobutene macromolecules have terminal double bonds to an extent of at least 50 mol %.

14 Claims, 2 Drawing Sheets

MIXTURE COMPRISING A DETERGENT AND A CO-DETERGENT

Figure 1:
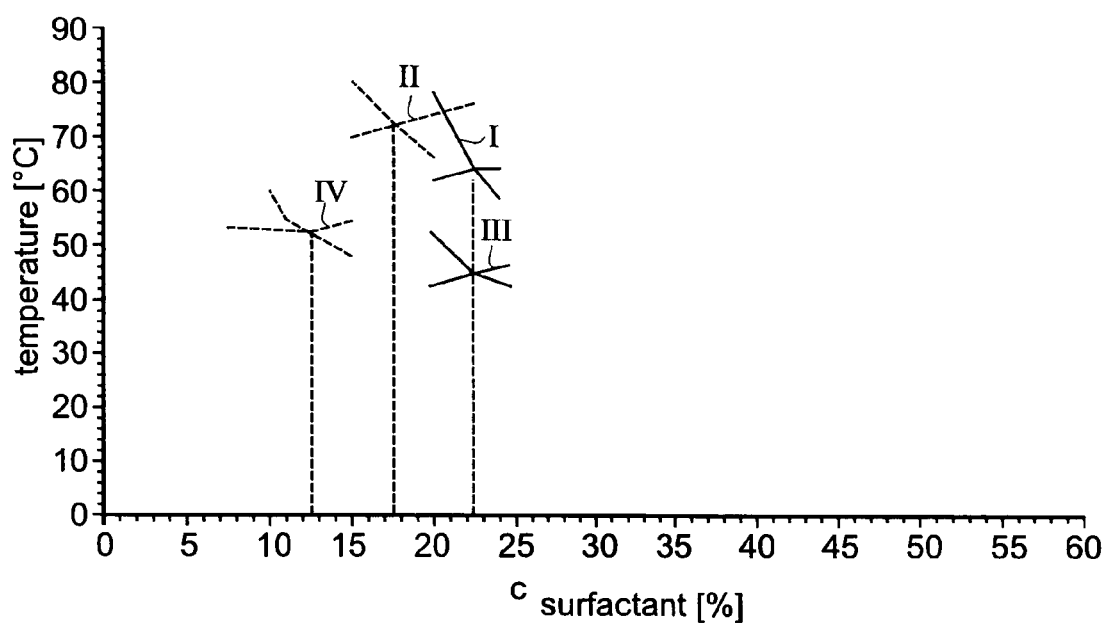

The invention relates to a mixture comprising a surfactant and a cosurfactant, to a microemulsion comprising a surfactant and a cosurfactant, to the use of a mixture or of a microemulsion, and to detergents, cleaners, wetting agents, coatings, adhesives, leather degreasing compositions, humectants or textile treatment compositions or pharmaceutical, crop protection or cosmetic formulation, in particular sunscreen, skincare or hair styling compositions, shower gels, shampoos, bath additives or scent oils.

Surfactants are substances which reduce the interfacial tension between liquid phases which are not miscible with one another, a polar phase, often water and a nonpolar, organic phase, and thus increase their mutual solubility. Surfactants have a characteristic structure and have at least one hydrophilic and one hydrophobic structural unit. This structure is also referred to as amphiphilic.

Surfactants are particularly relevant substances in ecological terms and their environmental compatibility must be ensured. As well as good degradability of surfactant residues in waste waters, it is therefore particularly important to reduce the amounts of surfactant used as far as possible without impairing their effectiveness, i.e. to increase the efficiency of the surfactants. In this connection, surfactant efficiency is usually used to refer to the amount of surfactant which is required in order to achieve a certain effect, for example in order to solubilize the fraction of nonpolar phase in the polar phase, or vice versa, or in order to reduce to the greatest possible extent the surface tension at the lowest possible concentration.

Customary conventional emulsions can comprise oil and water phases in very different fractions by volume. They have one continuous phase and one disperse phase, which is present as very small spheres which have been stabilized by coating with surfactants, in the continuous phase. Depending on the nature of the continuous phase, the emulsions are described as oil-in-water or water-in-oil. These emulsions are kinetically stable in the ideal case, i.e. they are retained even for a prolonged period, but not indefinitely. During temperature fluctuations in particular, they may have a tendency toward phase separation as a result of sedimentation, creaming, thickening or flocculation.

So-called microemulsions are thermodynamically stable, fluid, optically clear formulations of two immiscible liquids, such as oil and water. Microemulsions arise when a surfactant, or more frequently a mixture of a surfactant and a cosurfactant, reduces the oil/water interfacial tension to extremely low values, often in the range $10^{-3}$ to $10^{-9}$, preferably $10^{-4}$ to $10^{-6}$ N/m, such that the two insoluble phases remain dispersed by themselves in a homogeneous manner as a result of the thermal agitation. Microemulsions often have bicontinuous structures with equilibrium regions, so-called subphases in the order of magnitude from 100 to 1000 ångströms (cf. Advanced Materials, 2000, 12, No. 23, pages 1751 et seq.).

Bicontinuous microemulsions comprise two phases, a water phase and an oil phase, in the form of extended adjoining and intertwined domains at whose interface stabilizing interface-active surfactants are concentrated in a monomolecular layer. Bicontinuous micro emulsions form very readily, usually spontaneously due to the very low interfacial tension, when the individual components, water, oil and a suitable interface-active system, are mixed. Since the domains have only very small extensions in the order of magnitude of nanometers in at least one dimension, the microemulsions appear visually transparent and are thermodynamically, i.e. indefinitely, stable in a certain temperature range depending on the interface-active system used.

Bicontinuous microemulsions are described, for example, in the article "Mikroemulsionen—eine wissenschaftliche und anwendungstechnische Fundgrube?" [Microemulsions, a scientific and performance treasure trove?] by H.-F. Eicke in SÖFW-Journal 118 (1992), pages 311 to 314.

To achieve the required low interfacial tension at the phase boundaries, the microemulsions comprise special amphiphiles, i.e. interface-active agents, and electrolytes often dissolved in their aqueous phase and if appropriate further auxiliaries. Electrolytes are primarily added when the amphiphiles are partly or exclusively ionic surfactants.

It is known from DE-A 198 39 054 to increase the efficiency of surfactants by adding additives, the additives used being AB block copolymers with a water-soluble block A and a water-insoluble block B. The blocks A and B can here have molecular weights between 500 and 60 000 g/mol. As block A, preference is given to using a polyethylene oxide block, but generally all water-soluble blocks which form an amphiphile in combination with block B. For block B, polymers of a single monomer or a monomer mixture are described.

However, the described block copolymers have the disadvantage, in particular, that they are obtainable by preparation processes which are suitable for a laboratory scale, but not for large scale use. Said specification refers for the preparation process to DE-A 196 34 477, in which the polymerization using organo-alkali metals is described, i.e. a preparation method unsuitable for large-scale use.

It is an object of the present invention to provide substances which can be used as cosurfactants for increasing the efficiency of surfactants in emulsions, in particular in microemulsions, and which can be obtained in an economically advantageous manner on the basis of large-scale starting substances and by reaction pathways which can be realized on an industrial scale. In particular, the aim is to achieve an increase in the efficiency of surfactants in bicontinuous microemulsions.

The solution consists in a mixture comprising a surfactant and a cosurfactant, the cosurfactant being an amphiphilic polymer having one or more hydrophobic subunits (A) and one or more hydrophilic subunits (B), wherein one or more hydrophobic subunits (A) have been formed on the basis of a polyisobutene block whose polyisobutene macromolecules have terminal double bonds to an extent of at least 50 mol %.

It has surprisingly been found that amphiphilic polymers with the structure defined above are particularly suitable as cosurfactants in that they increase the efficiency of surfactants and are obtainable from large-scale and thus inexpensively obtainable substances by industrial reaction pathways. The amphiphilic polymers according to the invention are usually technical-grade mixtures of substances with a more or less broad molecular weight distribution.

In the context of the present invention, the term "a surfactant" and "a cosurfactant" are also understood in each case to mean mixtures of surfactants and of cosurfactants respectively.

Every hydrophobic subunit has preferably been formed from a polyisobutene block.

Polyisobutenes which correspond to the above definition, i.e. at least 50 mol % of which are formed from macromolecules having terminal double bonds, are referred to as so-called reactive polyisobutenes. The term terminal double bonds is understood as meaning both β-olefinic (vinyl) double bonds —[—CH=C(CH$_3$)$_2$] and α-olefinic (vinylidene) double bonds —[—C(CH$_3$)=CH$_2$]. Preferred reactive polyisobutenes are those in which at least 60 mol %, preferably at least 80 mol %, of the polyisobutene macromolecules, based on the total number of polyisobutene macromolecules, have terminal double bonds.

Suitable reactive polyisobutenes can be obtained, for example, by cationic polymerization of isobutene.

For the synthesis of suitable polyisobutenes, pure isobutene is preferably used. However, it is also possible in addition to use cationically polymerizable comonomers. However, the amount of comonomers should as a rule be less than 20% by weight, preferably less than 10% by weight and in particular less than 5% by weight.

Particularly suitable cationically polymerizable comonomers are vinylaromatics, such as styrene and α-methylstyrene, $C_1$-$C_4$-alkylstyrenes and 2-, 3- and 4-methylstyrene and 4-tert-butylstyrene, $C_3$- to $C_6$-alkenes, such as n-butene, isoolefins having 5 to 10 carbon atoms, such as 2-methylbut-1-ene, 2-methylpent-1-ene, 2-methylhex-1-ene, 2-ethylpent-1-ene, 2-ethylhex-1-ene and 2-propylhept-1-ene.

Suitable isobutene-containing feedstock for the process according to the invention are both isobutene itself and isobutene-containing $C_4$-hydrocarbon streams, for example refined $C_4$ fractions, $C_4$ cuts from isobutane dehydrogenation, $C_4$ cuts from steam crackers or so-called FCC crackers (FCC: fluid catalyzed cracking), provided that they have been substantially freed from 1,3-butadiene present therein. Typically, the concentration of isobutene in $C_4$-hydrocarbon streams is in the range from 40 to 60% by weight.

Suitable $C_4$-hydrocarbon streams should as a rule comprise less than 500 ppm, preferably less than 200 ppm, of 1,3-butadiene. The presence of but-1-ene and cis- and trans-but-2-ene is substantially noncritical for the polymerization and does not lead to losses of selectivity.

When $C_4$-hydrocarbon streams are used as feedstock, the hydrocarbons other than isobutene play the role of an inert solvent or are incorporated as comonomer in the form of polymerized units.

Suitable solvents are all organic compounds which are liquid in the chosen temperature range for the preparation of the polyisobutenes and neither eliminate protons nor have free electron pairs.

In particular, cyclic and acyclic alkanes, such as ethane, isopropane, n-propane and n-butane and its isomers, cyclopentane and n-pentane and its isomers, cyclohexane and n-hexane and its isomers, n-heptane and its isomers and higher homologs, cyclic and acyclic alkenes, such as ethene, isopropene, n-propene, n-butene, cyclopentene and n-pentene, cyclohexene and n-hexene, n-heptene, aromatic hydrocarbons, such as benzene, toluene or isomeric xylenes, may be mentioned. The hydrocarbons may also be halogenated. Examples of halogenated hydrocarbons comprise methyl chloride, methyl bromide, methylene chloride, methylene bromide, ethyl chloride, ethyl bromide, 1,2-dichloroethane, 1,1,1-trichloroethane, chloroform or chlorobenzene. Mixtures of the solvents may also be used, provided that no undesired properties occur.

It is particularly advisable with regard to process engineering to use solvents which boil in the desired temperature range. The polymerization is usually effected at from −80° C. to 0° C., preferably from −50° C. to −5° C. and particularly preferably at from −30° C. to −15° C.

Pure $BF_3$, its complexes with electron donors or mixtures thereof may be used as the catalyst. Electron donors (Lewis bases) are compounds which have a free electron pair, for example on an O, N, P or S atom, and can form complexes with Lewis acids. This complex formation is desired in many cases since the activity of the Lewis acid is thus reduced and secondary reactions are suppressed. Examples of suitable electron donors are ethers, such as diisopropyl ether or tetrahydrofuran, amines, such as triethylamine, amides, such as dimethylacetamide, alcohols, such as methanol, ethanol, isopropanol or tert-butanol. The alcohols also act as a proton source and thus initiate the polymerization. A cationic polymerization mechanism may also become active through protons from ubiquitous traces of water.

In the cationic polymerization under $BF_3$ catalysis, substantially linear polyisobutenes having a particularly high content of α-olefin groups at a chain end are obtained. When the reaction is effected in a suitable manner, the α-olefin content is not less than 80%.

Reactive polyisobutenes which have reactive α-olefin groups at both chain ends or which are branched can be particularly elegantly obtained by means of living cationic polymerization. However, linear polyisobutenes which have an α-olefin group only at one chain end can of course also be synthesized by this method.

In the living cationic polymerization, isobutene is polymerized with a suitable combination of an initiator molecule $IX_n$ with a Lewis acid S. Details of this method of polymerization are disclosed, for example, in Kennedy and Ivan, "Carbocationic Macromolecular Engineering", Hanser Publishers 1992.

Suitable initiator molecules $IX_n$ have one or more leaving groups X. The leaving group X is a Lewis base which may also be further substituted. Examples of suitable leaving groups comprise the halogens fluorine, chlorine, bromine and iodine, straight-chain and branched alkoxy groups, such as $C_2H_5O$—, n-$C_3H_7O$—, i-$C_3H_7O$—, n-$C_4H_9O$—, i-$C_4H_9O$—, sec-$C_4H_9O$— or t-$C_4H_9O$—, and straight-chain or branched carboxyl groups, such as $CH_3CO$—O—, $C_2H_5CO$—O—, n-$C_3H_7CO$—O—, i-$C_3H_7CO$—O—, n-$C_4H_9CO$—O—, i-$C_4H_9CO$—O—, sec-$C_4H_9CO$—O— or t-$C_4H_9CO$—O—. Associated with the leaving group or groups is the molecular moiety I, which can form sufficiently stable carbocations $I^+$ under reaction conditions. For initiating the polymerization, the leaving group is abstracted by means of a suitable Lewis acid S: I–X+S →$I^+$+$XS^-$ (shown here only for the case n=1). The resulting carbocation $I^+$ initiates the cationic polymerization and is incorporated into the resulting polymer. Suitable Lewis acids S are, for example, $AlY_3$, $TiY_4$, $BY_3$, $SnY_4$, $ZnY_2$, where Y is fluorine, chlorine, bromine or iodine. The polymerization reaction can be stopped by destroying the Lewis acid, for example by the reaction thereof with alcohol. The result is the formation of polyisobutene which has terminal —$C(CH_3)_2$-Z groups which can subsequently be converted into terminal α- and β-olefin groups.

Structures which can form tertiary carbocations are preferred as the initiator molecule. Particularly preferred are radicals which are derived from the lower oligomers of isobutene H—[$CH_2$—$C(CH_3)_2$]$_n$—X, where n is preferably from 2 to 5. Linear reactive polyisobutenes formed using such initiator molecules have a reactive group only at one end.

Linear polyisobutenes which have reactive groups at both ends can be obtained by using initiator molecules IXQ which have two leaving groups X and Q, where X and Q may be identical or different. In industry, compounds which comprise —$C(CH_3)_2$—X groups have proven useful. Examples comprise straight-chain or branched alkylene radicals $C_nH_{2n}$ (where n may preferably assume values of from 4 to 30), which may also be interrupted by a double bond or an aromatic, such as X—$(CH_3)_2$C—$CH_2$—$C(CH_3)_2$-Q, X—$(CH_3)_2$C—$CH_2$—C$(CH_3)_2CH_2$—$C(CH_3)_2$-Q, X—(CH₃)₂C—CH₂—C(CH₃)₂CH₂—C(CH₃)₂CH₂—C(CH₃)₂-Q or
X—(CH₃)₂C—CH₂—C(CH₃)₂CH₂—C(CH₃)₂CH₂—C(CH₃)₂—CH₂—C(CH₃)₂-Q,
X—(CH₃)₂C—CH═CH—C(CH₃)₂-Q or para and/or meta X—(CH₃)₂C—C₆H₄—C(CH₃)₂-Q.

Branched polyisobutenes can be obtained by using initiator molecules IX$_n$ which have 3 or more leaving groups, it being possible for the leaving groups to be identical or different. Examples of suitable initiator molecules comprise X—(CH₃)₂C—C₆H₃—[C(CH₃)₂-Q]-C(CH₃)₂—P as 1,2,4- and/or 1,3,5-isomer, where the leaving groups are preferably identical but may also be different. Further examples of mono-, di-, tri- or polyfunctional initiator molecules are to be found in the work by Kennedy and Ivan cited at the outset and in the literature cited there.

Suitable polyisobutenes are, for example, the Glissopal® brands from BASF AG, for example Glissopal 550, 1000, 1300 or 2300, and the Oppanol® brands from BASF AG, such as Oppanol B10 or B12.

Cosurfactants which have a polyisobutene block having a number-average molecular weight. M$_n$ in the range from 200 to 20 000 daltons, preferably in the range from 200 to 5000 daltons, are particularly suitable for the mixture according to the invention.

Depending on the polymerization process, the polydispersity index (PDI), i.e. the ratio of weight-average to number-average molecular weight, of the polyisobutenes which can preferably be used is in the range from 1.05 to 10, preferably in the range from 1.05 to 5, more preferably in the range from 1.05 to 2.0.

The method for determining the polydispersity (PDI) and for the number-average and weight-average molecular weight is described, for example, in Analytiker-Taschenbuch, Volume 4, pages 433 to 442, Berlin 1984.

The invention is in principle not limited with regard to the one or more hydrophilic subunits which can be used for the formation of the cosurfactant.

Subunits which are particularly readily soluble in water and particularly poorly soluble in oil are particularly advantageous.

One or more hydrophilic subunits (B₂) have preferably been formed from repeat ethylene oxide or ethylene oxide/propylene oxide units, preferably with a fraction of from 0 to 50% propylene oxide units, more preferably with a fraction of from 5 to 20% propylene oxide units. This may be a random copolymer, a gradient copolymer, an alternating or a block copolymer of ethylene oxide and propylene oxide.

One or more hydrophilic subunits (B₂) have more preferably been formed from monomer units selected from the following group: (meth)acrylic acid, including partly or completely neutralized (meth)acrylic acid, (meth)acrylates, vinyl acetate, vinyl alcohol, vinylpyrrolidone, polyallyl alcohol and hydrophilic derivatives of the monomer units listed above, or from mixtures thereof.

The hydrophobic and hydrophilic subunits forming the amphiphilic polymer are preferably linked by functionalizing the polyisobutene block, which forms the basis of the hydrophobic subunit(s), with introduction of polar groups and then modifying the functionalized polyisobutene block further if appropriate.

The degree of functionalization of the modified polyisobutene derivatives with terminal, polar groups is at least 65%, preferably at least 75% and most preferably at least 85%. In the case of the polymers having polar groups only at one chain end, this statement relates only to this one chain end. In the case of the polymers having polar groups at both chain ends and the branched products, this statement relates to the total number of chain ends. The unfunctionalized chain ends are both those which have no reactive group at all and those which have a reactive group but this was not reacted in the course of the functionalization reaction.

The term "polar group" is known to the person skilled in the art. The polar groups may be both protic and aprotic polar groups. The modified polyisobutenes thus have a hydrophobic molecular moiety comprising a polyisobutene radical and a molecular moiety which has at least a certain hydrophilic character, comprising terminal polar groups. They are preferably strongly hydrophilic groups. The terms "hydrophilic" and "hydrophobic" are known to the person skilled in the art.

Polar groups comprise, for example, sulfo radicals, carboxylic anhydrides, carboxyl groups, carboxamides, carboxylic esters, phosphonic acid groups, phosphonic esters and phosphonamides, hydroxyl groups, arylhydroxyl groups, arylphosphoric esters, arylsulfuric esters, polyoxyalkylene groups, polyoxyalkylene esters of said acid groups, amino groups, polyethyleneimino groups, amides of polyethyleneimines of said acids or epoxides, which may also be suitably substituted.

Suitable reactions for introducing polar groups (functionalization) are known in principle to the person skilled in the art.

In principle, the functionalization of the polyisobutenes used according to the invention can be carried out in one or more stages.

In a preferred embodiment, the functionalization of the polyisobutene used according to the invention is effected in one or more stages and is selected from:

i) reaction with aromatic hydroxyl compounds in the presence of an alkylation catalyst to obtain aromatic hydroxyl compounds alkylated with polyisobutenes,
ii) reaction of the polyisobutene block with a peroxy compound to obtain an epoxidized polyisobutene,
iii) reaction of the polyisobutene block with an alkene which has a double bond substituted by electron-attracting groups (enophile) in an ene reaction,
iv) reaction of the polyisobutene block with carbon monoxide and hydrogen in the presence of a hydroformylation catalyst to obtain a hydroformylated polyisobutene,
v) reaction of the polyisobutene block with a phosphorus halide or a phosphorus oxychloride to obtain a polyisobutene functionalized with phosphone groups,
vi) reaction of the polyisobutene block with a borane and subsequent oxidative cleavage to obtain a hydroxylated polyisobutene,
vii) reaction of the polyisobutene block with an SO₃ source, preferably acetyl sulfate or oleum, to obtain a polyisobutene with terminal sulfonic acid groups,
viii) reaction of the polyisobutene block with nitrogen oxides and subsequent hydrogenation to obtain a polyisobutene with terminal amino groups.

Re i): Alkylation of Aromatic Hydroxyl Compounds

For the derivatization, the reactive polyisobutene can be reacted with an aromatic hydroxyl compound in the presence of an alkylation catalyst. Suitable catalysts and reaction conditions of this so-called Friedel-Crafts alkylation are described, for example, in J. March, Advanced Organic Chemistry, 4th Edition, Verlag John Wiley & Sons, pages 534-539, which is hereby incorporated by reference.

The aromatic hydroxyl compound used for the alkylation is preferably selected from phenolic compounds having 1, 2 or 3 OH groups, which, if appropriate, may have at least one further substituent. Preferred further substituents are $C_1$-$C_8$-alkyl groups, in particular methyl and ethyl. Compounds of the general formula

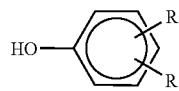

where $R^1$ and $R^2$, independently of one another, are hydrogen, OH or $CH_3$, are particularly preferred. Phenol, the cresol isomers, catechol, resorcinol, pyrogallol, fluoroglucinol and the xylenol isomers are particularly preferred. In particular, phenol, o-cresol and p-cresol are used. If desired, mixtures of the abovementioned compounds may also be used for the alkylation.

The catalyst is preferably selected from Lewis acid alkylation catalysts, which are understood in the context of the present application as meaning both individual acceptor atoms and acceptor-ligand complexes, molecules, etc., provided that they have overall (externally) Lewis acid (electron acceptor) properties. These include, for example, $AlCl_3$, $AlBr_3$, $BF_3$, $BF_3 2C_6H_5OH$, $BF_3[O(C_2H_5)_2]_2$, $TiCl_4$, $SnCl_4$, $AlC_2H_5Cl_2$, $FeCl_3$, $SbCl_5$ and $SbF_5$. These alkylation catalysts can be used together with a cocatalyst, for example an ether. Suitable ethers are di($C_1$-$C_8$-alkyl)ethers, such as dimethyl ether, diethyl ether and di-n-propyl ether, and tetrahydrofuran, di($C_5$-$C_8$-cycloalkyl)ethers, such as dicyclohexyl ether, and ethers having at least one aromatic hydrocarbon radical, such as anisole. If a catalyst-cocatalyst complex is used for the Friedel-Crafts alkylation, the molar ratio of catalyst to cocatalyst is preferably in a range from 1:10 to 10:1. The reaction can also be catalyzed with protic acids, such as sulfuric acid, phosphoric acid or trifluoromethanesulfonic acid. Organic protic acids may also be present in a form bound in a polymer, for example as ion exchange resin.

The alkylation can be carried out in the absence of a solvent or in a solvent. Suitable solvents are, for example, n-alkanes and mixtures thereof and alkylaromatics, such as toluene, ethylbenzene and xylene, and halogenated derivatives thereof.

The alkylation is preferably carried out at temperatures of from −10° C. to +100° C. The reaction is usually carried out at atmospheric pressure but can also be carried out at higher or lower pressures.

By a suitable choice of the molar ratios of aromatic hydroxyl compounds to polyisobutene and the catalyst, the intended proportion of alkylated products and the degree of alkylation thereof can be established. Thus, for example, substantially monoalkylated polyisobutenylphenols are generally obtained with an excess of phenol or in the presence of a Lewis acid alkylation catalyst if an ether is additionally used as cocatalyst.

The reaction of polyisobutenes with phenols in the presence of suitable alkylation catalysts is disclosed, for example, in U.S. Pat. No. 5,300,701 and WO 02/26840.

For the further functionalization, a polyisobutenylphenol obtained in step i) can be subjected to a reaction in the context of a Mannich reaction with at least one aldehyde, for example formaldehyde, and at least one amine which has at least one primary or secondary amine function, a compound alkylated with polyisobutene and additionally at least partly aminoalkylated being obtained. Reaction products and/or condensates of aldehyde and/or amine can also be used. The preparation of such compounds is described in WO 01/25 293 and WO 01/25 294, which are hereby incorporated by reference in their entirety.

Furthermore, a polyisobutenylphenol obtained in step i) can be alkoxylated with alkylene oxides, preferably ethylene oxide. In addition to ethylene oxide, the following pure alkylene oxides or mixtures can be used: propene oxide, 1-butene oxide, 2,3-butene oxide, 2-methyl-1,2-propene oxide (isobutene oxide), 1-pentene oxide, 2,3-pentene oxide, 2-methyl-1,2-butene oxide, 3-methyl-1,2-butene oxide, 2,3-hexene oxide, 3,4-hexene oxide, 2-methyl-1,2-pentene oxide, 2-ethyl-1,2-butene oxide, 3-methyl-1,2-pentene oxide, decene oxide, 4-methyl-1,2-pentene oxide, styrene oxide or a mixture of oxides from industrially available refined fraction streams.

In a further embodiment, the polyisobutenylphenols obtained are reacted with phosphorus oxychloride to obtain the aromatic phosphorus monoester. This is reacted in a subsequent step with polyethylenimines, alkylene oxides or polyalkylene oxides.

ii) Epoxidation

For the functionalization, the reactive polyisobutene can be reacted with at least one peroxy compound to obtain an epoxidized polyisobutene. Suitable epoxidation processes are described in J. March, Advanced Organic Chemistry, 4th Edition, Verlag John Wiley & Sons, pages 826-829, which is hereby incorporated by reference. At least one peracid, such as m-chloroperbenzoic acid, performic acid, peracetic acid, trifluoroperacetic acid, perbenzoic acid and 3,5-dinitroperbenzoic acid, is preferably used as the peroxy compound. The preparation of the peracids can be effected in situ from the corresponding acids and $H_2O_2$, if appropriate in the presence of mineral acids. Further suitable epoxidation reagents are, for example, alkaline hydrogen peroxide, molecular oxygen and alkyl peroxides, such as tert-butyl hydroperoxide. Suitable solvents for the epoxidation are, for example, conventional, nonpolar solvents. Particularly suitable solvents are hydrocarbons, such as toluene, xylene, hexane or heptane.

For the further functionalization, the epoxidized polyisobutenes which are obtained in step ii) can be reacted with ammonia, polyisobuteneaminoalcohols being obtained (EP-A 0 476 785).

In a further step, the epoxidized polyisobutenes obtained are reacted with said alkylene oxides. Ethylene oxide is preferred here.

iii) Ene Reaction

For the functionalization, the reactive polyisobutene can furthermore be reacted with at least one alkene which has an electron-poor double bond in an ene reaction (cf. for example DE-A 4 319 672 or H. Mach and P. Rath in "Lubrication Science II" (1999), pages 175-185, which is hereby incorporated by reference in its entirety). In the ene reaction, an alkene referred to as ene and having an allyl hydrogen atom is reacted with an electron-poor alkene, the so-called enophile, in a pericyclic reaction comprising a carbon-carbon linkage, a double bond shift and a hydrogen transfer. Here, the reactive polyisobutene reacts as an ene. Suitable enophiles are compounds as also used as dienophiles in the Diels-Alder reaction. Suitable enophiles are fumaroyl dichloride, fumaric acid, maleoyl dichloride, maleic anhydride and maleic acid, preferably maleic anhydride and maleic acid. Maleic anhydride is most preferably used as the enophile. Polyisobutenes functionalized with succinic anhydride groups (polyisobutenylsuccinic anhydride, PIBSA), as disclosed in EP-A 0 156 310, result.

The ene reaction can, if appropriate, be carried out in the presence of a Lewis acid as the catalyst. For example, aluminum chloride and ethylaluminum chloride are suitable.

In the reaction, a new α-olefin group is produced at the chain end. For the further functionalization, for example, a polyisobutene derivatized with succinic anhydride groups can be subjected to a subsequent reaction which is selected from:

a) reaction with at least one amine to obtain a polyisobutene at least partly functionalized with succinimide groups and/or succinamide groups,
b) reaction with at least one alcohol to obtain a polyisobutene functionalized with succinic ester groups,
c) reaction with at least one alkylene oxide to obtain a polyisobutene functionalized with two succinic ester groups (per succinic anhydride group),
d) reaction with maleic anhydride to obtain a product having two succinic anhydride groups at the chain end (so-called PIBSA),
e) hydrolysis to obtain a polyisobutene functionalized with succinic acid groups, the succinic acid groups being reacted with alkylene oxides as under c),
f) if free carboxyl groups are still present after the reaction of the succinic anhydride group, they can also be converted into salts. Suitable cations in salts are especially alkali metal cations, ammonium ions and alkylammonium ions.

Re a) and b)

For the further derivatization, the succinic anhydride groups can, for example, be reacted with polar reactants, such as alcohols or amines. Suitable polar reactants are preferably primary alcohols ROH or primary amines $RNH_2$ or secondary amines RR'NH, where R is a linear or branched saturated hydrocarbon radical which carries at least one substituent selected from the group consisting of OH, $NH_2$ or $NH_3^+$ and, if appropriate, one or more CH(O) groups and, if appropriate, has nonneighboring —O— and/or —NH— and/or tertiary —N-groups, and R', independently of R, has the same meaning. Here, both carboxyl groups of the succinic anhydride may react or only one group may react while the other carboxyl group is present as a free acid group or as a salt. The above substituents may also be further modified, for example by alkoxylation.

Further synthesis variants for the derivatization of succinic anhydride groups are mentioned in the applications having the application numbers DE 101 251 58.0 and DE 101 476 50.7.

It is also known to the person skilled in the art that a succinic anhydride group can be converted under suitable conditions into a succinimide group.

In a further embodiment, reactive polyisobutene can be subjected to free radical copolymerization with maleic anhydride (cf. WO 95/07944, WO 01/55059, WO 90/03359). The strictly alternating copolymers thus obtained can be further reacted as described above. The reactions with alkylene oxides, polyalkylene oxides or polyethylenimines are preferred.

iv) Hydroformylation

For the functionalization, the reactive polyisobutene can be subjected to a reaction with carbon monoxide and hydrogen in the presence of a hydroformylation catalyst, a hydroformylated polyisobutene being obtained.

Suitable catalysts for the hydroformylation are known and preferably comprise a compound or a complex of an element of subgroup VII of the Periodic Table of the Elements, such as Co, Rh, Ir, Ru, Pd or Pt. For influencing the activity and/or selectivity, hydroformylation catalysts modified with N- or P-containing ligands are preferably used. Suitable salts of these metals are, for example, the hydrides, halides, nitrates, sulfates, oxides, sulfides or the salts with alkyl- or arylcarboxylic acids or alkane- or arylsulfonic acids. Suitable complex compounds have ligands which are selected, for example, from halides, amines, carboxylates, acetylacetonate, aryl- or alkanesulfonates, hydride, CO, olefins, dienes, cycloolefins, nitriles, N-containing heterocycles, aromatics and heteroaromatics, ethers, $PF_3$, phospholes, phosphabenzenes and mono-, bi- and polydentate phosphine, phosphinite, phosphonite, phosphoramidite and phosphite ligands.

In general, catalytically active species of the general formula $H_xM_y(CO)_zL_q$, where M is a metal of subgroup VIII, L is a ligand and q, x, y and z are integers dependent on the valency and type of the metal and the coordination number of the ligand L, are formed under hydroformylation conditions from the catalysts or catalyst precursors used in each case.

According to a preferred embodiment, the hydroformylation catalysts are prepared in situ in the reactor used for the hydroformylation reaction.

Another preferred form is the use of a carbonyl generator in which carbonyl produced beforehand is adsorbed, for example onto active carbon, and only the desorbed carbonyl is fed to the hydroformylation but not the salt solutions from which the carbonyl is produced.

Rhodium compounds or complexes suitable as catalysts are, for example, rhodium(II) and rhodium(III) salts, such as rhodium(III) chloride, rhodium(III) nitrate, rhodium(III) sulfate, potassium rhodium sulfate, rhodium(II) or rhodium(II) carboxylate, rhodium(III) and rhodium(III) acetate, rhodium (III) oxide, salts of rhodium(III) acid, trisammonium hexachlororhodate(III), etc. Rhodium complexes, such as biscarbonylrhodium acetylacetonate, acetylacetonatobisethylenerhodium(I), etc., are furthermore suitable.

Also suitable are ruthenium salts or compounds. Suitable ruthenium salts are, for example, ruthenium(III) chloride, ruthenium(IV), ruthenium(VI) or ruthenium(VIII) oxide, alkali metal salts of the ruthenium oxyacids, such as $K_2RuO_4$ or $KRuO_4$, or complex compounds, such as, for example, $RuHCl(CO)(PPh_3)_3$. The metal carbonyls of ruthenium, such as trisrutheniumdodecacarbonyl and hexarutheniumoctadecacarbonyl, or mixed forms in which CO is partly replaced by ligands of the formula $PR_3$, such as $Ru(CO)_3(PPh_3)_2$, can also be used.

Suitable cobalt compounds are, for example, cobalt(I) chloride, cobalt(II) sulfate, cobalt(II) carbonate, cobalt(II) nitrate, the amine or hydrate complexes thereof, cobalt carboxylates, such as cobalt formate, cobalt acetate, cobalt ethylhexanoate, cobalt naphthanoate, and the cobalt-caprolactamate complex. Here too, the carbonyl complexes of cobalt, such as dicobaltoctacarbonyl, tetracobaltdodecacarbonyl and hexacobalthexadecacarbonyl, can be used.

Said compounds and further suitable compounds are in principle known and are sufficiently described in the literature.

Suitable activating agents which can be used for the hydroformylation are, for example, Brønsted acids, Lewis acids, such as $BF_3$, $AlCl_3$ and $ZnCl_2$, and Lewis bases.

The composition of the synthesis gas used, comprising carbon monoxide and hydrogen, can be varied within wide ranges. The molar ratio of carbon monoxide to hydrogen is as a rule from about 5:95 to 95:5, preferably from about 40:60 to 60:40. The temperature during the hydroformylation is in general in a range of from about 20 to 200° C., preferably from about 50 to 190° C. The reaction is carried out as a rule at the partial pressure of the reaction gas at the chosen reaction temperature. In general, the pressure is in a range from about 1 to 700 bar, preferably from 1 to 300 bar.

The carbonyl number of the hydroformylated polyisobutenes obtained depends on the number-average molecular weight $M_n$. Products having a number-average molecular weight $M_n$ of 10 000 daltons preferably have carbonyl numbers of from 2 to 5.6 mg KOH/g, in particular from 3.6 to 5.6 mg KOH/g. Products having a number-average molecular weight. $M_n$ of 40 000 daltons have carbonyl numbers of from 0.5 to 1.4 mg KOH/g, in particular from 0.9 to 1.4 mg KOH/g. The carbonyl numbers of products having other molecular weights can be determined by interpolation or extrapolation.

The predominant part of the double bonds present in the medium molecular weight, reactive polyisobutene used is preferably converted into aldehydes by the hydroformylation. By using suitable hydroformylation catalysts and/or an excess of hydrogen in the synthesis gas used, the predominant part of the ethylenically unsaturated double bonds present in the starting material can also be converted directly into alcohols (cf. for example DE-A 100 03 105). This can also be effected in a two-stage functionalization according to reaction step B) described below.

The functionalized polyisobutenes obtained by hydroformylation are advantageously suitable as intermediates for further processing by functionalization of at least a part of the aldehyde functions present in them.

A) Oxo Carboxylic Acids

For the further functionalization, the hydroformylated polyisobutenes obtained in step iv) can be reacted with an oxidizing agent to obtain a polyisobutene at least partly functionalized with carboxyl groups.

For the oxidation of aldehydes to carboxylic acids, it is possible in general to use a large number of different oxidizing agents and oxidation processes, which are described, for example, in J. March, Advanced Organic Chemistry, Verlag John Wiley & Sons, 4th Edition, page 701 et seq. (1992). These include, for example, the oxidation with permanganate, chromate, atmospheric oxygen, etc. The oxidation with air/oxygen can be effected both catalytically in the presence of metal salts and in the absence of catalysts. Preferably used metals are those which are capable of a valency change, such as Cu, Fe, Co, Mn, etc. The reaction also takes place as a rule in the absence of a catalyst. In the case of atmospheric oxidation, the conversion can easily be controlled by means of the duration of the reaction.

According to a further embodiment, the oxidizing agent used is an aqueous hydrogen peroxide solution in combination with a carboxylic acid, such as, for example, acetic acid. The acid number of the polyisobutenes having a carboxyl function which are obtained depends on the number-average molecular weight $M_n$. Products having a number-average molecular weight $M_n$ of 10 000 daltons preferably have acid numbers of from 2 to 5.6 mg KOH/g, in particular from 3.6 to 5.6 mg KOH/g. Products having a number-average molecular weight $M_n$ of 40 000 daltons have acid numbers of from 0.5 to 1.4 mg KOH/g, in particular from 0.9 to 1.4 mg KOH/g. The acid numbers of products having other molecular weights can be determined by interpolation or extrapolation.

The polyisobutenes having a carboxyl function which are obtained can be reacted in a further reaction step. Reactions may be those with alkylene oxides, esterifications with polyalkylene oxides or amide formation with polyethylenimines.

B) Oxo Alcohols

According to a further suitable embodiment, the hydroformylated polyisobutenes obtained in step iv) can be subjected to a reaction with hydrogen in the presence of a hydrogenation catalyst to obtain a polyisobutene which is at least partly functionalized with alcohol groups.

Suitable hydrogenation catalysts are in general transition metals, such as Cr, Mo, W, Fe, Rh, Co, Ni, Pd, Pt, Ru, etc., or mixtures thereof, which, in order to increase the activity and stability, can be applied to supports, such as active carbon, alumina, kieselguhr, etc. In order to increase the catalytic activity, Fe, Co and preferably Ni, also in the form of the Raney catalysts, can be used as metal sponge having a very large surface area.

The hydrogenation of the oxo aldehydes from stage iv) is effected, depending on the activity of the catalyst, preferably at elevated temperatures and superatmospheric pressure. The reaction temperature is preferably from about 80 to 150° C. and the pressure from about 50 to 350 bar.

The alcohol number of the resulting polyisobutenes having hydroxyl groups depends on the number-average molecular weight. $M_n$. Products having a number-average molecular weight $M_n$ of 10 000 daltons preferably have alcohol numbers of from 2 to 5.6 mg KOH/g, in particular from 3.6 to 5.6 mg KOH/g. Products having a number-average molecular weight $M_n$ of 40 000 daltons have alcohol numbers of from 0.5 to 1.4 mg KOH/g, in particular from 0.9 to 1.4 mg KOH/g. The alcohol numbers of products having other molecular weights can be determined by interpolation or extrapolation.

The polyisobutenes functionalized with alcohol groups can additionally be alkoxylated with alkylene oxides, preferably ethylene oxide.

C) Amine Synthesis

According to a further suitable embodiment, the hydroformylated polyisobutenes obtained in step iv) are subjected, for the further functionalization, to a reaction with hydrogen and ammonia or a primary or secondary amine in the presence of an amination catalyst to obtain a polyisobutene which is at least partly functionalized with amino groups.

Suitable amination catalysts are the hydrogenation catalysts described above in stage B), preferably copper, cobalt or nickel, which can be used in the form of the Raney metals or on a support. Platinum catalysts are also suitable.

In the amination of ammonia, aminated polyisobutenes having primary amino functions are obtained. Primary and secondary amines suitable for the amination are compounds of the general formulae R—$NH_2$ and RR'NH, where R and R', independently of one another, are, for example, $C_1$-$C_{10}$-alkyl, $C_6$-$C_{20}$-aryl, $C_7$-$C_{20}$-arylalkyl, $C_7$-$C_{20}$-alkylaryl or cycloalkyl.

The amine number of the polyisobutenes having an amino function which are obtained depends on the number-average molecular weight $M_n$. Products having a number-average molecular weight $M_n$ of 10 000 daltons preferably have amine numbers of from 2 to 5.6 mg KOH/g, in particular from 3.6 to 5.6 mg KOH/g. Products having a number-average molecular weight $M_n$ of 40 000 daltons have amine numbers of from 0.5 to 1.4 mg KOH/g, in particular from 0.9 to 1.4 mg KOH/g. The amine numbers of products having other molecular weights can be determined by interpolation or extrapolation.

The polyisobutenes functionalized with amino groups can additionally be alkoxylated with alkylene oxides, preferably ethylene oxide.

V) Preparation of Phosphonic Acid Derivatives

For the functionalization, the reactive polyisobutene can be subjected to a reaction with $PX_5$ (X=Cl, Br, I) to obtain a polyisobutene functionalized with a phosphonyl halide group. For the further functionalization and hence for permitting grafting, the derivatized polyisobutene is subjected to a subsequent reaction which is selected from:

a) reaction with at least one amine or polyethylenimine to obtain a polyisobutene which is at least partly functionalized with phosphonamide groups,
b) reaction with at least one alcohol or polyalkylene oxide to obtain a polyisobutene functionalized with phosphonic ester groups,
c) reaction with at least one alkylene oxide to obtain a polyisobutene functionalized with phosphonic ester groups,
d) hydrolysis to obtain a polyisobutene functionalized with phosphonic acid groups, the phosphonic acid groups being reacted with alkylene oxides as under c),
e) if, after the reaction of the phosphonyl halide group, free acid groups are still present they can also be converted into salts. Suitable cations in salts are especially alkali metal cations, ammonium ions and alkylammonium ions.

vi) Hydroboration

For the functionalization, the reactive polyisobutene can be subjected to a reaction with a borane (if appropriate, produced in situ), a hydroxylated polyisobutene being obtained.

Suitable hydroboration processes are described in J. March, Advanced Organic Chemistry, 4th Edition, Verlag John Wiley & Sons, pages 783-789, which is hereby incorporated by reference. Suitable hydroboration reagents are, for example, diborane, which as a rule is produced in situ by reacting sodium borohydride with $BF_3$ etherate, diisoamylborane(bis[3-methylbut-2-yl]borane), 1,1,2-trimethylpropylborane, 9-borobicyclo[3.3.1]nonane, diisocamphenylborane, which are obtainable by hydroboration of the corresponding alkenes with diborane, chloroboranedimethyl sulfide, alkyldichloroboranes or $H_3B$—$N(C_2H_5)_2$.

Usually, the hydroboration is carried out in a solvent. Suitable solvents for the hydroboration are, for example, acyclic ethers, such as diethyl ether, methyl tert-butyl ether, dimethoxyethane, diethylene glycol dimethyl ether, triethylene glycol dimethyl ether, cyclic ethers, such as tetrahydrofuran or dioxane, and hydrocarbons, such as hexane or toluene, or mixtures thereof. The reaction temperature is determined as a rule by the reactivity of the hydroboration agent and is usually from the melting point to the boiling point of the reaction mixture, preferably in the range from 0° C. to 60° C.

Usually, the hydroboration agent is used in excess, based on the alkene. The boron atom preferably undergoes addition at the less substituted and hence sterically less hindered carbon atom.

Usually, the alkylboranes formed are not isolated but are converted directly into the desired products by subsequent reaction. A very significant reaction of the alkylboranes is the reaction with alkaline hydrogen peroxide to obtain an alcohol, which preferably formally corresponds to the anti-Markovnikov hydroxylation of the alkene.

The polyisobutenes functionalized with alcohol groups can additionally be alkoxylated with alkylene oxides, preferably ethylene oxide.

vii) Reaction with an $SO_3$ Source

For the functionalization, the reactive polyisobutene can furthermore be reacted with an $SO_3$ source, a polyisobutene with terminal sulfonic acid groups being formed.

The polyisobutenes functionalized with sulfonic acid groups can be prepared by reacting the reactive polyisobutenes with an $SO_3$ source. Suitable $SO_3$ sources are a mixture of sulfur trioxide and air, sulfur trioxide hydrates, sulfur trioxide-amine complexes, sulfur trioxide-ether complexes, sulfur trioxide-phosphate complexes, oleum, acetyl sulfate, a mixture of sulfur trioxide and acetic anhydride, sulfamic acid, alkyl sulfates or chlorosulfonic acids. The reaction can be effected either in the absence of a solvent or in any desired inert anhydrous solvent. Suitable reaction temperatures are in the range from −30° C. to +200° C. and are dependent on the sulfonation reagent used. For example, a sulfonation with acetyl sulfate is effected at low temperatures, and elevated temperatures should be avoided, since otherwise decomposition of the product can occur. The sulfonation reagent is generally used in a molar ratio to polyisobutene of from 1:1 to 2:1. Acetyl sulfate or a mixture of sulfuric acid and acetic anhydride, acetyl sulfate being formed in situ, is preferably used, the polyisobutene functionalized with sulfonic acid groups being formed directly. Others of said sulfonation reagents, for example the mixture of sulfur trioxide and oxygen, can initially form an intermediate sultone, which has to be hydrolyzed to the desired sulfonic acid. A process for the preparation of polyisobutenes functionalized with sulfonic acid groups is disclosed, for example, in WO 01/70830.

The polyisobutenes functionalized with sulfonic acid groups are reacted with alkylene oxides, polyalkylene oxides or polyethylenimines.

If free acid groups are still present after the functionalization, they can also be converted into the salt form. Suitable cations in salts are especially alkali metal cations, ammonium ions and alkylammonium ions.

viii) Functionalization with Amino Groups

For the functionalization, the reactive polyisobutene can be reacted with nitrogen oxides, polyisobutenes with terminal amino groups being obtained after subsequent hydrogenation.

Suitable nitrogen oxides are, for example, NO, $NO_2$, $N_2O_3$, $N_2O_4$, mixtures of these nitrogen oxides with one another and mixtures of these nitrogen oxides with oxygen. Mixtures of NO and $NO_2$ with oxygen are particularly preferred. Furthermore, the nitrogen oxides can additionally comprise inert gases, e.g. nitrogen. The reaction of the polyisobutenes with the nitrogen oxides is effected in general at a temperature of from −30 to +150° C. in an inert organic solvent. The products obtained are then hydrogenated, preferably by catalytic hydrogenation with hydrogen in the presence of hydrogenation catalysts. The hydrogenation is generally carried out in a temperature range from 20 to 250° C., depending on the reduction system used. The hydrogenation pressure in the catalytic hydrogenation is in general from 1 bar to 300 bar. A process for the preparation of polymers terminated with amino groups is disclosed, for example, in WO 97/03946.

The polyisobutenes functionalized with amino groups can additionally be alkoxylated with alkylene oxides, preferably ethylene oxide.

If acid groups (carboxyl, phosphonic acid, phosphoric acid or sulfuric acid groups) are reacted with polyalkylene oxides, it is possible to use polyalkylene oxides such as, for example, polyethylene oxide, polypropylene oxide, mixed copolymers of EO and PO, monoalkylpolyethylene oxide (alkyl=methyl-, ethyl-, $C_{12}$—, $C_{18}$—, etc.), monoaminoethylene oxide, etc. The reactions of the acid groups with these alkylene oxides are so-called polymer-analogous reactions (esterifications). The length of the alkylene oxide chain can be from 3 to 400 units.

The cosurfactants to be used in the mixtures according to the invention preferably have an AB structure.

Further preferred structures of the cosurfactant are $A_pB_q$ where p and q are independently from 1 to 8, or comb structures comprising $A_2$ and $B_2$.

As well as the cosurfactants described above, the mixture according to the invention comprises a surfactant. This may be a mixture of surfactants. In principle, any surfactant from any of the known surfactant groups or any mixture of ionic or nonionic surfactants can be used.

The proportion of the cosurfactant, based on the surfactant, is preferably in the range from 0.01 to 99.99%, in particular between 1 and 50%, particularly preferably between 5 and 25%.

Depending on the field of use of the mixtures according to the invention, suitable surfactants are, for example, all classical cleaning surfactants, or food-approved surfactants, such as Tweens® or Spans®. As far as the surfactant classes are concerned, nonionic, anionic, cationic, amphoteric surfactants are suitable; in particular also polymer surfactants, peptide surfactants, silicone surfactants, amino acid-based surfactants, sugar surfactants, fat-based surfactants, gemini surfactants, amine oxides, amidoamine oxides, alkylbetaines, ether carboxylates, amphoacetates, alkyl sulfates or sulfosuccinates.

Suitable anionic surfactants are, for example, fatty alcohol sulfates or fatty alcohols having 8 to 22, preferably 10 to 18, carbon atoms, for example $C_9$- to $C_{11}$-alcohol sulfates, $C_{12}$- to $C_{13}$-alcohol sulfates, cetyl sulfate, myristyl sulfate, palmityl sulfate, stearyl sulfate and tallow fatty alcohol sulfate.

Further suitable anionic surfactants are sulfated ethoxylated $C_8$- to $C_{22}$-alcohols (alkyl ether sulfates) or soluble salts thereof. Compounds of this type are prepared, for example, by firstly alkoxylating a $C_8$- to $C_{22}$-, preferably a $C_{10}$- to $C_{18}$-, alcohol, for example a fatty alcohol, and then sulfating the alkoxylation product. For the alkoxylation, preference is given to using ethylene oxide, employing 2 to 50, preferably 3 to 20, mol of ethylene oxide per mole of fatty alcohol. The alkoxylation of the alcohols can, however, also be carried out with propylene oxide on its own and optionally butylene oxide. Also suitable are those alkoxylated $C_8$- to $C_{22}$-alcohols which comprise ethylene oxide and propylene oxide or ethylene oxide and butylene oxide. The alkoxylated $C_8$- or to $C_{22}$-alcohols can comprise the ethylene oxide, propylene oxide and butylene oxide units in the form of blocks or in random distribution.

Also suitable are alkanesulfonates, such as $C_8$- to $C_{24}$-, preferably $C_{10}$- to $C_{18}$-, alkanesulfonates, and soaps, such as Na or K salts of $C_8$- to $C_{24}$-carboxylic acids.

Further suitable anionic surfactants are N-acylsarcosinates with aliphatic saturated or unsaturated $C_8$- to $C_{25}$-acyl radicals, preferably $C_{10}$- to $C_{20}$-acyl radicals, for example N-oleoylsarcosinate.

In addition, the mixtures according to the invention can comprise $C_{10}$- to $C_{13}$-linear and/or slightly branched alkylbenzenesulfonates (LAS).

The anionic surfactants are added to the mixture, preferably in the form of salts. Suitable cations in these salts are alkali metal salts, such as sodium, potassium and lithium and ammonium salts, such as, for example hydroxyethylammonium, di(hydroxyethyl)ammonium and tri(hydroxyethyl)ammonium salts.

Suitable nonionic surfactants are, in particular:
alkoxylated $C_8$- to $C_{22}$-alcohols such as fatty alcohol alkoxylates or oxo alcohol alkoxylates. These may be alkoxylated with ethylene oxide, propylene oxide and/or butylene oxide. Surfactants which may be used here are all alkoxylated alcohols which comprise at least two added molecules of one of the alkylene oxides specified above. In this connection, block polymers of ethylene oxide, propylene oxide and/or butylene oxide are suitable or addition products which comprise said alkylene oxides in random distribution. The nonionic surfactants comprise, per mole of alcohol, generally 2 to 50, preferably 3 to 20, mol of at least one alkylene oxide. These preferably comprise ethylene oxide as alkylene oxide. The alcohols preferably have 10 to 18 carbon atoms. Depending on the nature of the alkoxylation catalyst used in the preparation, the alkoxylates have a broad or narrow alkylene oxide homolog distribution;

alkylphenol alkoxylates, such as alkylphenol ethoxylates with $C_6$- to $C_{14}$-alkyl chains and 5 to 30 alkylene oxide units;

alkyl polyglucosides having 8 to 22, preferably 10 to 18, carbon atoms in the alkyl chain and generally 1 to 20, preferably 1.1 to 5, glucoside units sorbitan alkanoates, also alkoxylated;

N-alkylglucamides, fatty acid alkoxylates, fatty acid amine alkoxylates, fatty acid amide alkoxylates, fatty acid alkanolamide alkoxylates, alkoxylated, block copolymers of ethylene oxide, propylene oxide and/or butylene oxide, polyisobutene ethoxylates, polyisobutene-maleic anhydride derivatives, monoglycerides, also alkoxylated, and bisglycerides.

Particularly suitable nonionic surfactants are alkyl alkoxylates or mixtures of alkyl alkoxylates, as are described, for example, in DE-A 102 43 363, DE-A 102 43 361, DE-A 102 43 360, DE-A 102 43 365, DE-A 102 43 366, DE-A 102 43 362 or in DE-A 43 25 237. These are alkoxylation products which have been obtained by reacting alkanols with alkylene oxides in the presence of alkoxylation catalysts, or are mixtures of alkoxylation products. Particularly suitable starter alcohols are the so-called Guerbet alcohols, in particular ethylhexanol, propylheptanol and butyloctanol. Particular preference is given to propylheptanol. Preferred alkylene oxides are propylene oxide and ethylene oxide, with alkyl alkoxylates with a direct bond of a preferably short polypropylene oxide block to the starter molecular, as are described, for example, in DE-A 102 43 365, being preferred in particular on the basis of their low residual alcohol content and their good biodegradability.

Alkoxylation catalysts which may be used are bases, for example alkali metal hydroxides or alkali metal alkoxides, but also Lewis acids, for example $BF_3$, $SbCl_5$, $SnCl_4 \times 2H_2O$, $BF_3 \times H_3BO_4$, or $BF_3$ dietherate. Particularly suitable alkoxylation catalysts are double hydroxide clays, such as hydrotalcite, which may, in particular, be modified with additives, as described in DE-A 43 25 237.

Depending on the choice of alkoxylation catalyst, specific properties of the alkoxylates result in each case, in particular with regard to the distribution of the degree of alkoxylation. For example, if the last-mentioned double-hydroxide clays are used, the alkoxylation products obtained have a narrow molecular weight distribution or homolog distribution and are particularly suitable for use in the mixtures according to the invention with cosurfactants.

The advantageous properties described above, in particular with regard to the degree of alkoxylation, are also achieved through the use of double metal cyanide (DMC) compounds, as are described, for example, in DE-A 102 43 361 as alkoxylation catalysts.

The invention also provides for the use of a mixture comprising a surfactant and an above-described cosurfactant for stabilizing emulsions, in particular microemulsions. In the present context, stabilization means that the efficiency of surfactants is increased through the addition of cosurfactants, i.e. the solubilization of a defined oil/water mixture is made possible under defined conditions with a relatively small amount of surfactant.

The above-described cosurfactants are particularly preferably suitable for stabilizing microemulsions, i.e. for shifting the so-called X point, which represents the lowest concentration of surfactant at a given temperature from which the thermodynamic state of the microemulsion, i.e. the single-phase state when examined microscopically, arises.

The mixtures according to the invention can in principle be used in all areas where emulsions play a role, for example in the fields of application listed in DE-A 101 18 480 for mixtures comprising a surfactant and an AB block copolymer as additive (cosurfactant), which also comprise additives whose efficiency can be increased by the surfactant/additive system: for example as crop restoration, growth or crop protection compositions, products with microbiocidal active ingredients, products with positively or negatively acting microorganisms, in particular with a content of enzymes, cleaners and/or care compositions for the home and for commercial purposes, disinfectants, hair, bodycare or cleansing compositions, automobile cleaning, care and/or preservation compositions, textile treatment compositions, leather and/or fur care compositions, as paints, coatings, medicaments, construction aids, toothpastes or mouthwashes.

Synergistic effects, as are described in DE-A 101 18 480 for the surfactant/AB block copolymer system in combination with additional biocides, microorganisms and/or any other active ingredients, are achieved correspondingly for systems comprising the mixtures according to the invention comprising a surfactant and a cosurfactant, and corresponding additives, in particular biocides, microorganisms and/or any other active ingredients.

The invention also provides a microemulsion comprising a surfactant and a cosurfactant, as defined above.

The mixtures or microemulsions according to the invention are optimally suitable for the uptake and release of hydrophobic substances, in particular the use as detergent, emulsifier, foam regulator, wetting agent for hard surfaces or as reaction medium for organic, inorganic, bioorganic or photochemical reactions.

Preference is given to use in detergents, surfactant formulations for the cleaning of hard surfaces, humectants, cosmetic, pharmaceutical and crop protection formulations, paints, coatings, adhesives, leather degreasing compositions, formulations for the textile industry, fiber processing, metal processing, food industry, water treatment, paper industry, fermentation, mineral processing, fire protection or in emulsion polymerizations.

The invention further provides detergents, cleaners, wetting agents, coatings, adhesives, leather degreasing compositions, humectants or textile treatment compositions or pharmaceutical, crop protection or cosmetic formulation, in particular sunscreen, skincare or hair styling compositions, shower gels, shampoos, bath additives or scent oils comprising, as well as customary ingredients, a mixture comprising a surfactant and a cosurfactant as described above or a microemulsion comprising a surfactant and a cosurfactant.

The invention will be illustrated in detail below with reference to a drawing and to use examples.

Figure 2:
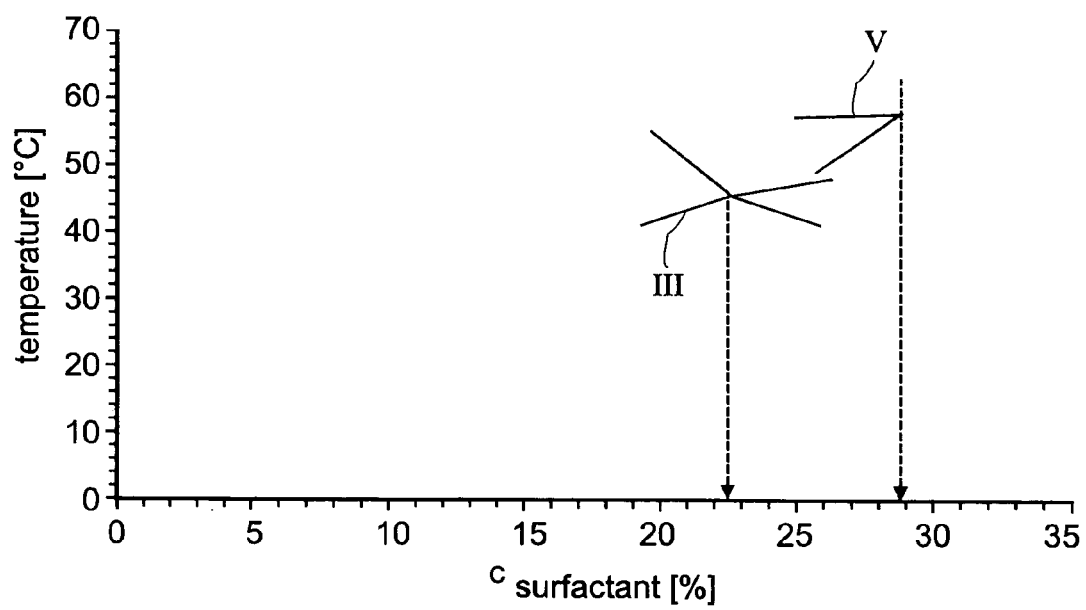

In the drawing, specifically:

FIG. 1 shows the influence of the surfactant (prepared in DMC catalysis or not) on the shifting of the X point and FIG. 2 shows the influence of unfunctionalized polyisobutene on the shifting of the X point of the same microemulsion.

As is well known, the X point indicates the minimum concentration of surfactant at a given temperature from which the water and the n-decane phase are entirely miscible for a given reference system (water/n-decane in the present case) and a given surfactant (Lutensol® ON50 from BASF AG in the present case) and form a thermodynamically stable microemulsion without excess water or oil phase.

USE EXAMPLE 1

Influence of the Surfactant on the X Point

In the figure appended, the concentration of the surfactant (Lutensol® ON50 from BASF AG) is shown on the abscissa, in the figure with $c_{surfactant}$, in % by weight, and the temperature in ° C. is shown on the ordinate. Sections from the particular phase diagrams ("fish phase diagrams") have been prepared for said 1:1 water/n-decane reference system under I and III for comparison, i.e. without addition of a cosurfactant, and under II and IV as inventive use examples with addition of 10% by weight in each case of PIB-OH1000, ethoxylated with 82 ethylene oxide units. Diagram I was obtained with the surfactant Lutensol® ON50 from BASF AG, diagram III with a Lutensol® ON50 which was obtained in DMC catalysis. The figure shows that the shifting of the X point for a surfactant not prepared in DMC catalysis (shifting of I to II), with addition of the same amount of cosurfactant is only 5%, compared to a shift (of III to IV) by 7.5% in the case of use of a surfactant with narrow homolog distribution which has been obtained in DMC catalysis.

USE EXAMPLE 2 (COMPARATIVE)

Influence of Unfunctionalized Polyisobutene on the X Point

The "fish phase diagram III" corresponds to the phase diagram described above under use example 1 for Lutensol® ON50 from BASF AG.

For comparison, unfunctionalized polyisobutene was added, i.e. polyisobutene with unconverted double bonds. The resulting phase diagram V shows that this shifts the X point to higher surfactant concentrations, i.e. that the efficiency of the surfactant worsens. The use example thus shows that the use of polyisobutenes which do not correspond to the subject matter of the present patent application lead to worsening of the efficiency of surfactants. The invention, in contrast, starts from polyisobutene blocks which have at least 50 mol % of terminal double bonds, i.e. from so-called reactive polyisobutene.

We claim:

1. A method of stabilizing an emulsion comprising adding, during preparation of the emulsion, a surfactant and a cosurfactant, the cosurfactant being an amphiphilic polymer having one or more hydrophobic subunits (A) and one or more hydrophilic subunits (B), wherein one or more of said hydrophobic subunits (A) have been formed on the basis of a polyisobutene block whose polyisobutene macromolecules have terminal double bonds to an extent of at least 50 mol %, wherein the amount of cosurfactant added is from 0.01 to 25% by weight of the amount of surfactant added.

2. The method according to claim 1, wherein every hydrophobic subunit (A) has been formed on the basis of a polyisobutene block whose polyisobutene macromolecules have terminal double bonds to an extent of at least 50 mol %.

3. The method according to claim 1, wherein said polyisobutene block has been formed from polyisobutene macromolecules of which at least 60 mol % based on the total number of polyisobutene macromolecules, have terminal double bonds.

4. The method according to claim 1, wherein said polyisobutene block has a number-average molecular weight Mn in the range from 200 to 20,000 daltons.

5. The method according to claim 1, wherein said polyisobutene block has a polydispersity index (PDI) in the range from 1.05 to 10.

6. The method according to claim 1, wherein one or more of said hydrophilic subunits (B) have been formed from repeat ethylene oxide units or ethylene oxide/propylene oxide units.

7. The method according to claim 1, wherein one or more of said hydrophilic subunits (B) have been formed from monomer units selected from the group consisting of (meth) acrylic acid, (meth)acrylates, vinyl acetate, vinyl alcohol, vinylpyrrolidone, allyl alcohol, styrene, hydrophilic derivatives of the listed monomer units, and mixtures thereof.

8. The method according to claim 1, wherein said polyisobutene block is functionalized by the introduction of polar groups and the functionalized polyisobutene block is optionally modified further.

9. The method according to claim 8, wherein the functionalization of the polyisobutene block is carried out by a reaction which is selected from the group consisting of:
   i) a reaction with aromatic hydroxyl compounds in the presence of an alkylation catalyst to obtain aromatic hydroxyl compounds alkylated with polyisobutenes,
   ii) a reaction of the polyisobutene block with a peroxy compound to obtain an epoxidized polyisobutene,
   iii) a reaction of the polyisobutene block with an alkene which has an electron-poor double bond (enophile) in an ene reaction,
   iv) a reaction of the polyisobutene block with carbon monoxide and hydrogen in the presence of a hydroformylation catalyst to obtain a hydroformylated polyisobutene,
   v) a reaction of the polyisobutene block with a phosphorus halide or a phosphorus oxychloride to obtain a polyisobutene functionalized with phosphone groups,
   vi) a reaction of the polyisobutene block with a borane and subsequent oxidative cleavage to obtain a hydroxylated polyisobutene,
   vii) a reaction of the polyisobutene block with an $SO_3$ source to obtain a polyisobutene with terminal sulfonic acid groups, and
   viii) a reaction of the polyisobutene block with nitrogen oxides and subsequent hydrogenation to obtain a polyisobutene with terminal amino groups.

10. The method according to claim 1, wherein said cosurfactant has an $A_pB_q$ structure where p and q are each independently an integer from 1 to 8, or a comb structure composed of A and B.

11. The method according to claim 1, wherein said surfactant is a surfactant with narrow homolog distribution.

12. The method according to claim 1, wherein the emulsion is a microemulsion.

13. The method according to claim 12, wherein said surfactant is a surfactant with narrow homolog distribution or one obtained under DMC catalysis.

14. A detergent, cleaner, wetting agent, coating, adhesive, leather degreasing composition, humectant or textile treatment composition or a pharmaceutical, crop protection or cosmetic formulation, selected from the group consisting of sunscreen, skincare and hair styling composition, shower gel, shampoo, bath additive and scent oil, comprising an emulsion stabilized according to claim 1.

* * * * *